United States Patent [19]

Nasu et al.

[11] Patent Number: 5,399,767
[45] Date of Patent: Mar. 21, 1995

[54] PROCESS FOR PRODUCING 3,5-DIFLUORANILINE

[75] Inventors: Rikuo Nasu; Motohiko Hamaguchi, both of Yokkaichi, Japan

[73] Assignee: Ishihara Sangyo Kaisha Ltd., Osaka, Japan

[21] Appl. No.: 194,625

[22] Filed: Feb. 8, 1994

Related U.S. Application Data

[63] Continuation of Ser. No. 827,080, Jan. 28, 1992, abandoned.

[30] Foreign Application Priority Data

Jan. 28, 1991 [JP] Japan .................... 3-087169

[51] Int. Cl.$^6$ .......................................... C07C 209/74
[52] U.S. Cl. ................................. 564/412; 564/442
[58] Field of Search ........................... 564/412, 442

[56] References Cited

U.S. PATENT DOCUMENTS

| | | | |
|---|---|---|---|
| 4,085,141 | 4/1978 | Wedemeyer | 260/570 R |
| 4,206,147 | 6/1980 | Daumas et al. | 260/578 |
| 4,618,686 | 10/1986 | Boyer | 549/360 |
| 4,692,554 | 9/1987 | Yamaguchi | 564/430 |
| 5,068,392 | 11/1991 | McKendry et al. | 560/46 |
| 5,089,653 | 2/1992 | Pews et al. | 560/47 |
| 5,162,584 | 11/1992 | Moilliet et al. | 564/442 |
| 5,336,808 | 8/1994 | Krishnamurti et al. | 564/412 |

FOREIGN PATENT DOCUMENTS

| | | |
|---|---|---|
| 0045709 | 2/1982 | European Pat. Off. . |
| 0415595 | 3/1991 | European Pat. Off. . |

OTHER PUBLICATIONS

Chemical Abstracts, vol. 66, No. 15, Apr. 10, 1967, abstract No. 65202z, p. 6118, N. Ishikawa, et al., "2,4,6--Trichloro-3,5-Difluoroaniline and its Derivatives".

*Primary Examiner*—Glennon H. Hollrah
*Assistant Examiner*—B. Burn
*Attorney, Agent, or Firm*—Oblon, Spivak, McClelland, Maier & Neustadt

[57] ABSTRACT

A process for producing 3,5-difluoroaniline, which comprises reacting a benzonitrile compound of the formula (I):

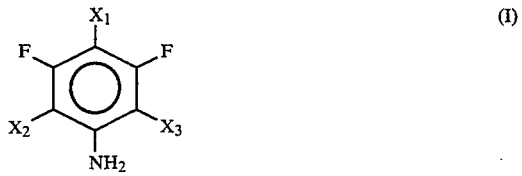

(I)

wherein each of $X_1$, $X_2$ and $X_3$ is hydrogen, chlorine, bromine or a cyano group, provided that at least one of $X_1$ to $X_3$ is a cyano group, with a mineral acid for hydrolysis and decarboxylation to obtain an aniline compound of the formula (II):

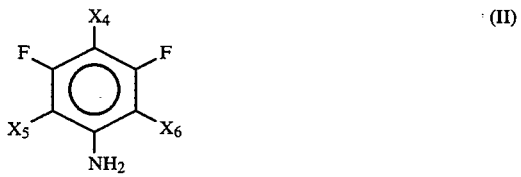

(II)

wherein each of $X_4$, $X_5$ and $X_6$ is hydrogen, chlorine or bromine, provided that at least one of $X_4$ to $X_6$ is hydrogen, and in the case of a compound of the formula (II) wherein $X_4$, $X_5$ and $X_6$ are not simultaneously hydrogen, reacting such a compound with hydrogen in a presence of a catalyst for reduction to obtain 3,5-difluoroaniline.

4 Claims, No Drawings

PROCESS FOR PRODUCING 3,5-DIFLUORANILINE

This application is a continuation of application Ser. No. 07/827,080, filed on Jan. 28, 1992, now abandoned.

The present invention relates to a process for industrially advantageously producing 3,5-difluoroaniline which is useful as an intermediate for pharmaceuticals or agricultural chemicals.

As a process for producing 3,5-difluoroaniline, a process is conceivable which comprises firstly preparing 1-bromo-3,5-difluorobenzene or 1,3,5-trifluorobenzene as an intermediate and then reacting ammonia thereto to obtain 3,5-difluoroaniline. As a method for producing this intermediate, a method of isomerizing 1-bromo-2,4-difluorobenzene in the presence of an alkali metal amide to obtain 1-bromo-3,5-difluorobenzene, or a method of fluorinating 1,3,5-trichlorobenzene with potassium fluoride in a solvent to obtain 1,3,5-trifluorobenzene, is known.

However, the above-mentioned process, particularly the method for producing the intermediate, has a difficulty in its practical industrial use, since the alkali metal amide used for the isomerization reaction is likely to explode, and its handling is dangerous. On the other hand, the fluorination reaction also has a difficulty in its practical industrial application, since the reaction time is long, and the yield is low in spite of the fact that strict reaction conditions are required.

The present inventors have found it possible to produce desired 3,5-difluoroaniline industrially advantageously by using inexpensive materials which are readily available in a large amount as starting materials and by employing a combination of reaction steps with high reaction yields under relatively mild reaction conditions by a simple reaction operation. The present invention has been accomplished on the basis of this discovery.

Thus, the present invention provides a process for producing 3,5-difluoroaniline, which comprises reacting a benzonitrile compound of the formula (I):

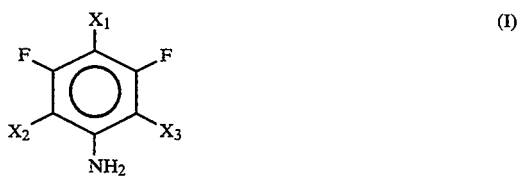

wherein each of $X_1$, $X_2$ and $X_3$ is hydrogen, chlorine, bromine or a cyano group, provided that at least one of $X_1$ to $X_3$ is a cyano group, with a mineral acid for hydrolysis and decarboxylation to obtain an aniline compound of the formula (II):

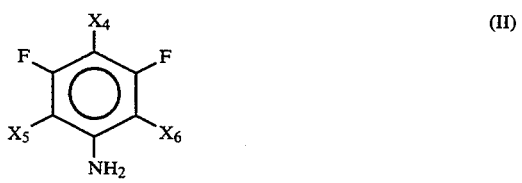

wherein each of $X_4$, $X_5$ and $X_6$ is hydrogen, chlorine or bromine, provided that at least one of $X_4$ to $X_6$ is hydrogen, and in the case of a compound of the formula (II) wherein $X_4$, $X_5$ and $X_6$ are not simultaneously hydrogen, reacting such a compound with hydrogen in a presence of a catalyst for reduction to obtain 3,5-difluoroaniline.

Now, the present invention will be described in detail with reference to the preferred embodiments.

The above benzonitrile compound includes, for example, 4-amino-2,6-difluorobenzonitrile, 2-amino-4,6-difluorobenzonitrile, 4-amino-3-chloro-2,6-difluorobenzonitrile, 4-amino-3,5-dichloro-2,6-difluorobenzonitrile, 2-amino-3,5-dichloro-4,6-difluorobenzonitrile, 4-amino-2,6-difluoroisophthalonitrile, 4-amino-5-chloro-2,6-difluoroisophthalonitrile, 4-amino-5-bromo-2,6-difluoroisophthalonitrile and 2-amino-4,6-difluoro-1,3,5-tricyanobenzene. Among them, 4-amino-2,6-difluorobenzonitrile, 2-amino-4,6-difluorobenzonitrile, 4-amino-2,6-difluoroisophthalonitrile or 2-amino-4,6-difluoro-1,3,5-tricyanobenzene gives desired 3,5-difluoroaniline directly only by the reaction for hydrolysis and decarboxylation. Among the above benzonitrile compounds, 4-amino-3,5-dichloro-2,6-difluorobenzonitrile, 2-amino-3,5-dichloro-4,6-difluorobenzonitrile or 4-amino-5-chloro-2,6-difluoroisophthalonitrile, particularly 4-amino-5-chloro-2,6-difluoroisophthalonitrile is preferred, since it is inexpensive and available in a large amount and has high reactivity.

The aniline compound includes, for example, 2-chloro-3,5-difluoroaniline, 2,6-dichloro-3,5-difluoroaniline, 2,4-dichloro-3,5-difluoroaniline and 2-bromo-3,5-difluoroaniline. Among them, 2-chloro-3,5-difluoroaniline, 2,6-dichloro-3,5-difluoroaniline or 2,4-dichloro-3,5-difluoroaniline, particularly 2-chloro-3,5-difluoroaniline, is preferred from the viewpoint of industrial availability.

The above benzonitrile compound can be prepared by various methods. A suitable method is employed depending upon the type of the particular compound. Typical examples will be given hereinafter.

(A) Fluorination Step

Using as a starting material a compound of the above formula (I) wherein the fluorine and the amino group are replaced by chlorine or bromine, such as pentachlorobenzonitrile or tetrachloroisophthalonitrile, such a compound is reacted with potassium fluoride to substitute the chlorine or bromine by fluorine. In this fluorination reaction, the reaction proceeds under relatively mild reaction conditions to give the desired product in good yield, since the compound of the formula (I) has at least one cyano group and has chlorine or bromine at the o- or p-position to this cyano group.

The potassium fluoride to be used here, is preferably the one having a small particle size and a large specific surface area and being thoroughly dried so that it has high reactivity. This reaction is conducted in an open system or a closed system under an inert atmosphere such as nitrogen gas. In the reaction in an open system, a solvent may be employed. As such a solvent, an aprotic polar solvent such as dimethylsulfoxide, sulforane or N,N-dimethylformamide, may be mentioned. Depending upon the starting material or the type of the solvent, an phase transfer catalyst may be employed. As the phase transfer catalyst, a phosphonium compound such as tetraphenyl phosphonium bromide or hexadecyltributylphosphonium iodide, or a quaternary ammonium salt such as tetrabutyl ammonium bromide, may be mentioned. Also in the reaction in a closed system, xylene or benzonitrile may be used as a solvent, but the desired reaction usually proceeds without using such a solvent.

The amount of the potassium fluoride and the amounts of the solvent and the catalyst when they are used, can not generally be defined, since they vary depending upon the differences in e.g. the types of the starting materials and the reaction conditions. However, in the case of pentachlorobenzonitrile or tetrachloroisophthalonitrile, from 3 to 6 mols of potassium fluoride, from 1 to 10 mols of the solvent and from 0.005 to 0.2 mol of the catalyst may usually be used per mol of such a starting material. The reaction temperature is usually from 70° to 220° C. in the case of the open system reaction and from 180° to 400° C. in the case of the closed system reaction. The reaction is usually completed in from 0.5 to 24 hours. After the reaction, the product is subjected to conventional post-treatment to obtain desired 3,5-dichloro-2,4,6-trifluorobenzonitrile or 5-chloro-2,4,6-trifluoroisophthalonitrile as a fluorinated product in good yield. The desired product can be obtained, for example, in a yield of at least 80% and with a purity of at least 95%.

(B) Amination Step

The fluorinated product obtained by the above fluorination step, is reacted with ammonia to aminate only one fluorine. The reaction of the fluorinated product with ammonia is conducted in accordance with a conventional amination reaction in which a halogen is substituted by an amino group. The amination reaction proceeds under relatively mild reaction conditions, since the fluorinated product has at least one cyano group and has fluorine to be aminated, at the o- or p-position to the cyano group.

For this amination reaction, a solvent may be used as the case requires. For example, the above fluorinated product may be dissolved in a solvent, and ammonia gas may be blown thereinto, or a 5 to 40% ammonium aqueous solution may be added thereto, whereby the reaction readily proceeds. As the solvent, benzene, toluene, acetonitrile or N,N-dimethylformamide may be mentioned. The amounts of ammonia and the solvent can not generally be defined. Usually however, the former is used in an amount of from 1 to 20 mols as $NH_3$, per mol of the fluorinated product, and the latter is used in an amount of from 1,000 to 10,000 parts by weight, per 1,000 parts by weight of the fluorinated product. If the amount of ammonia departs substantially from the above-mentioned range, there will be a problem such that the reaction will not sufficiently proceed, or the reaction will proceed excessively.

Likewise, the reaction temperature and the reaction time for this amination reaction can not generally be defined. However, in the case of 3,5-dichloro-2,4,6-trifluorobenzonitrile or 5-chloro-2,4,6-trifluoroisophthalonitrile, the reaction temperature is usually from −30° to +40° C., preferably from −10° C. to room temperature, and the reaction time is usually from 0.5 to 24 hours. In this amination reaction, like the amination reaction of 3,5-dichloro-2,4,6-trifluorobenzonitrile, a mixture of 4-amino-3,5-dichloro-2,6-difluorobenzonitrile and 2-amino-3,5-dichloro-4,6-difluorobenzonitrile will be formed, and such a mixture may be supplied to the next step of hydrolysis and decarboxylation as it is. After the reaction, the reaction product is subjected to conventional post-treatment, whereby the desired benzonitrile compound can be obtained, for example, in a yield of at least 90% with a purity of at least 95%.

Now, with respect to the process for producing 3,5-difluoroaniline of the present invention, the step of hydrolysis and decarboxylation and the step of reduction will be described with reference to general embodiments.

(1) Step of Hydrolysis and Decarboxylation

This step of hydrolysis and decarboxylation can be easily conducted by reacting the benzonitrile compound of the above formula (I) with a mineral acid. The reaction conditions and the reaction operation may be those commonly employed for the conventional hydrolysis of cyano groups, followed by a decarboxylation step. For example, the desired reaction proceeds by heating and stirring the benzonitrile compound together with an aqueous mineral acid solution.

As the mineral acid to be used here, sulfuric acid or phosphoric acid may be mentioned. Preferred is sulfuric acid. The amount of the mineral acid varies depending upon the type of the starting material and the reaction conditions and can not generally be defined. However, it is used in an amount of from 2.0 to 10 mols per mol (as calculated by the cyano group) of the benzonitrile compound, and for example, when sulfuric acid is used, it is employed in the form of an aqueous solution having a concentration of from 20 to 98%. The reaction temperature and the reaction time for this hydrolysis and decarboxylation, can not generally be defined. However, the former is usually from 100° to 180° C., and the latter is usually from 1 to 30 hours.

After the reaction, the reaction product is subjected to conventional post-treatment, whereby an aniline compound of the above formula (II) may be obtained, for example, in a yield of at least 70% with a purity of at least 95%. In a case where a compound of the formula (I) wherein each of $X_1$ to $X_3$ is not chlorine or bromine, is used as the above benzonitrile compound, it is of course possible to directly produce desired 3,5-difluoroaniline by this hydrolysis and decarboxylation reaction, whereby the subsequent reduction step can be omitted.

(2) Step of Reduction

This reduction step is conducted by reacting the aniline compound of the above formula (II) with hydrogen in the presence of a catalyst and in the presence or absence of a basic substance. Here, while maintaining fluorine in the structural formula of the aniline compound, chlorine and/or bromine is substituted by hydrogen to obtain desired 3,5-difluoroaniline. The reaction conditions and the reaction operation may be those commonly used in a conventional step of reduction of chlorine and/or bromine with hydrogen. In this reduction step, hydrogen gas may directly be used. However, a substance capable of generating hydrogen in the reaction system, such as formic acid or hydrazine, may also be used.

As the catalyst to be used for this reduction step, a catalyst having platinum, palladium, nickel or copper, preferably platinum or palladium, as the catalyst component, supported on a carrier, such as a platinum catalyst supported on alumina, a palladium catalyst supported on carbon or a nickel.copper or Raney nickel catalyst supported on active carbon, may be mentioned. Among them, a platinum catalyst supported on alumina or a palladium catalyst supported on carbon is preferred. The amount of the catalyst varies depending upon the type of the starting materials and the reaction conditions and can not generally be defined. However, for example, a 5% palladium.carbon catalyst is usually used in an amount of from 0.02 to 20 parts by weight, per 100 parts by weight of the aniline compound.

As the basic substance to be used here, a hydroxide or carbonate of an alkali metal, such as sodium hydroxide, potassium hydroxide, sodium carbonate or potassium carbonate, may be mentioned. Further, a tertiary amine such as trimethylamine or triethylamine, or an amine such as hydrazine, may be mentioned. However, an alkali metal hydroxide or a tertiary amine is preferred. The amount of the basic substance to be used, can not generally be defined. However, it is usually from 1.0 to 10.0 mols per mol of the aniline compound. Here, a solvent such as water or a lower alkanol such as methanol or ethanol, may be used as the case requires.

This reduction reaction is conducted usually under a hydrogen gas pressure of from 1 to 50 atm at a reaction temperature of from room temperature to 150° C. after introducing the above aniline compound, the catalyst, the basic substance and water into a closed container and supplying hydrogen gas thereto. In the case where formic acid or hydrazine is substantially used instead of hydrogen gas, the reduction reaction is conducted usually under atmospheric pressure or elevated pressure at a reaction temperature of from room temperature to 150° C. Thus, the reaction is completed usually in from 0.5 to 24 hours. After completion of the reaction, the reaction product is subjected to conventional post-treatment, whereby desired 3,5-difluoroaniline can be produced, for example, in a yield of at least 75% with a purity of at least 98%.

Now, the process of the present invention will be described with reference to Examples. However, it should be understood that the present invention is by no means restricted by such specific Examples.

EXAMPLE 1

(a) Step of Fluorination

Into a 500 ml four necked flask equipped with a stirrer, a condenser and a thermometer, 100 g (0.376 mol) of tetrachloroisophthalonitrile, 300 g of N,N-dimethylformamide and 72 g (1.24 mol) of spray dried potassium fluoride were charged and stirred under a nitrogen gas atmosphere at 110° C. and reacted for one hour. The reaction solution was analyzed by gas chromatography, whereby the conversion of the starting material was 100% and the selectivity for 5-chloro-2,4,6-trifluoroisophthalonitrile was 97%.

The reaction mixture was cooled, and potassium chloride formed by the reaction and unreacted potassium fluoride were separated by filtration, and a filtrate was washed with 100 g of N,N-dimethylformamide. Then, the filtrate including the washed solution was put into 1 l of water, and the precipitated solid was collected by filtration, washed with water and dried to obtain 74.5 g (purity: 98%, yield: 89.7%) of 5-chloro-2,4,6-trifluoroisophthalonitrile was obtained. The mass spectrum analytical result of this product is shown below.

Mass: m/e 216(M+), 181(M+-Cl)

(b) Step of Amination

Into a 500 ml four necked flask equipped with a stirrer, a condenser, a thermometer and a dropping funnel, 74.5 g (purity: 98%, 0.337 mol) of 5-chloro-2,4,6-trifluoroisophthalonitrile and 150 ml of N,N-dimethylformamide were charged, and while cooling to 0° C. under stirring, 40.9 g (0,674 mol) of 28% aqueous ammonia was dropwise added from the dropping funnel. The reaction solution was maintained at a temperature of from −10° to 0° C. and reacted for one hour. After completion of the reaction, the reaction solution was analyzed by gas chromatography, whereby the conversion of the starting material was 100%, and the yield of 4-amino-5-chloro-2,6-difluoroisophthalonitrile was 97%.

The reaction solution was put into 1,000 ml of water, and the precipitated crystals were collected by filtration. Further, the crystals were washed with water and dried to obtain 69.6 g (yield: 94.8%, purity: 98%) of 4-amino-5-chloro-2,6-difluoroisophthalonitrile.

The mass spectrum analytical result of this product is shown below.

Mass: m/e 213(M+), 178(M+-Cl)

(c) Step for Hydrolysis and Decarboxylation

Into a 300 ml four necked flask equipped with a stirrer, a condenser and a thermometer, 69.6 g (purity: 98%, 0.32 mol) of 4-amino-5-chloro-2,6-difluoroisophthalonitrile and 179.2 g of a 70% sulfuric acid aqueous solution were introduced, heated under stirring and reacted at 150° C. for 3 hours. The reaction solution was analyzed by gas chromatography, whereby the conversion of the starting material was 100%, and the yield of 2-chloro-3,5-difluoroaniline was 98%.

The reaction solution was carefully introduced into ice water, neutralized by an addition of sodium hydroxide and extracted with methylene chloride. The extract was dried over anhydrous sodium sulfate. Then, the solvent was distilled off, and the residue was distilled under reduced pressure to obtain 45.4 g (yield: 85%, purity: 98%) of 2-chloro-3,5-difluoroaniline.

The mass spectrum analytical result of this product is shown below.

Mass: m/e 163 (M+), 144(M+-F), 128(M+-Cl)

(d-1) Step of Reduction

Into a 500 ml SUS autoclave, 45.4 g (purity: 98%, 0.272 mol) of 2-chloro-3,5-difluoroaniline, 1.84 g of 5% palladium-carbon, 30.2 g (0.299 mol) of triethylamine and 45.4 g of water were introduced, and hydrogen gas was sealed in. Then, the mixture was reacted under a hydrogen gas pressure of 15 kg/cm² at a temperature of 100° C. for 4 hours. Then, the reaction solution was cooled to 50° C. Then, palladium-carbon was filtered off, and 50 g of a 25% sodium hydroxide aqueous solution was added. The mixture was stirred and left to stand still. Then, the oil layer was separated. Then, this oil layer was distilled to recover 28.5 g of triethylamine, and then 32.3 g (purity: 99%, yield: 91.0%) of 3,5-difluoroaniline was obtained.

(d-2) Step of Reduction

Into a 100 ml four necked flask equipped with a stirrer, a condenser and a thermometer, 8.2 g (purity: 98%, 0.05 mol) of 2-chloro-3,5-difluoroaniline, 1.0 g of 5% palladium-carbon, 20 g of ethyleneglycol monomethyl ether and 18.8 g (0.3 mol) of 80% hydrazine monohydrate were introduced. Then, the mixture was reacted at 100° C. for 20 hours under stirring. Then, the reaction solution was analyzed by gas chromatography, whereby the conversion of the starting material was 91%, and the yield of 3,5-difluoroaniline was 89.6%.

The reaction solution was cooled and put into a mixture of water and methylene chloride. Then, palladium-carbon was filtered off and the oil layer was separated. Then, this oil layer was distilled to obtain 5.1 g (purity: 98%, yield: 77%) of 3,5-difluoroaniline.

EXAMPLE 2

(a) Step of Fluorination

Into a 500 ml four necked flask equipped with a stirrer, a condenser and a thermometer, 100 g (0.363 mol) of pentachlorobenzonitrile, 7.6 g (0.0182 mol) of tetraphenylphosphonium bromide, 300 g of sulforane and 14.7 g (1.63 mol) of spray dried potassium fluoride were charged and stirred under a nitrogen gas atmosphere at a temperature of from 170° to 180° C. and reacted for 6 hours. The reaction solution was analyzed by gas chromatography, whereby the conversion of the starting material was 100%, and the selectivity for 3,5-dichloro-2,4,6-trifluorobenzonitrile was 96%.

The reaction mixture was cooled, and potassium chloride formed by the reaction and unreacted potassium fluoride were separated by filtration and a filtrate was washed with 100 g of warmed sulforane. Then, the filtrate including the washed solution was distilled under reduced pressure to obtain 68.1 g (yield: 81.3%) of 3,5-dichloro-2,4,6-trifluorobenzonitrile distilled under an absolute pressure of 20 mmHg at a temperature of from 109° to 110° C. From the gas chromatography analysis, the purity was found to be 98%.

(b) Step of Amination

Into a 500 ml four necked flask equipped with a stirrer, a condenser and a thermometer, 68.1 g (purity: 98%, 0.3 mol) of 3,5-dichloro-2,4,6-trifluorobenzonitrile and 200 ml of acetonitrile were introduced, and 182 g (3.0 mol) of 28% aqueous ammonia was added under stirring and cooling. Then, the mixture was reacted at room temperature for 10 hours. After completion of the reaction, the reaction solution was analyzed by gas chromatography, whereby the conversion of the starting material was 99%, the yield of 4-amino-3,5-dichloro-2,6-difluorobenzonitrile was 69%, and the yield of 2-amino-3,5-dichloro-4,6-difluorobenzonitrile was 30%.

This reaction solution was put into 1,000 ml of water, and the precipitated crystals were collected by filtration. Further, the crystals were washed with water and dried to obtain 63.6 g (yield: 95%) of a benzonitrile mixture containing 69% of 4-amino-3,5-dichloro-2,6-difluorobenzonitrile and 30% of 2-amino-3,5-dichloro-4,6-difluorobenzonitrile.

The mass spectrum analytical result of this product is shown below.

Mass: m/e 222(M+), 187(M+-Cl), 152(M+-2Cl)

(c) Step for Hydrolysis and Decarboxylation

Into a 300 ml four necked flask equipped with a stirrer, a condenser and a thermometer, 63.6 g of the benzonitrile mixture obtained in the above amination step and 165.1 g of a 80% sulfuric acid aqueous solution were introduced, heated under stirring and reacted at 150° C. for 24 hours. The reaction solution was analyzed by gas chromatography, whereby the conversion of the starting material was 100%, and the yield of 2,6-dichloro-3,5-difluoroaniline was 59%, and the yield of 2,4-dichloro-3,5-difluoroaniline was 29%.

After cooling, the reaction solution was put into ice water and neutralized by an addition of sodium hydroxide and extracted with methylene chloride. The extract was dried over anhydrous sodium sulfate. Then, the solvent was distilled off, and the residue was distilled under reduced pressure to obtain 50.8 g (yield: 88.3%) of an aniline mixture containing 68% of 2,6-dichloro-3,5-difluoroaniline and 29% of 2,4-dichloro-3,5-difluoroaniline.

The mass spectrum analytical result of this product is shown below.

Mass: m/e 197(M+), 178(M+-F), 162(M+-Cl)

(d) Step of Reduction

Into a 500 ml SUS autoclave, 49.5 g (0.243 mol) of the aniline mixture obtained in the above hydrolysis and decarboxylation step, 2.0 g of 5% palladium-carbon and 194.4 g of a 10% sodium hydroxide aqueous solution were charged, and hydrogen gas was sealed in. Then, the mixture was reacted under a hydrogen gas pressure of 15 kg/cm$^2$ at a temperature of 100° C. for 3 hours. Then, the reaction solution was cooled to 50° C., and palladium-carbon was filtered off. The oil layer was separated to obtain 31.5 g (purity: 95%, remaining starting material: 0.7%, as analyzed by gas chromatography) of crude 3,5-difluoroaniline. Then, this oil layer was distilled to obtain 29.0 g (yield: 90%) of 3,5-difluoroaniline having a purity of at least 98%.

The physical properties of this product are shown below.

Boiling point: 81°-82° C./20 mmHg
Melting point: 40°-42° C.

According to the present invention, 3,5-difluoroaniline useful as an intermediate material for pharmaceuticals or agricultural chemicals can be produced industrially advantageously.

We claim:

1. A process for producing 3,5-difluoroaniline, which comprises reducing an aniline compound of the formula (II)

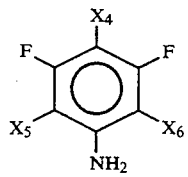

wherein each of $X_4$, $X_5$ and $X_6$ is hydrogen, chlorine or bromine, provided that at least one of $X_4$ to $X_6$ is chlorine or bromine, with hydrogen in the presence of (i) a catalyst selected from the group consisting of platinum and palladium and (ii) a base selected from the group consisting of an alkali metal hydroxide, an alkali metal carbonate, and an amine, at a temperature of from room temperature to 150° C. under atmospheric pressure or elevated pressure. to obtain 3,5-difluoroaniline.

2. A process for producing 3,5-difluoroaniline, which comprises reacting a compound selected from the group consisting of 2-chloro-3,5-difluoroaniline, 2,6-dichloro-3,5-difluoroaniline and 2,4-dichloro-3,5-difluoroaniline with hydrogen in the presence of (i) a catalyst selected from the group consisting of platinum and palladium and (ii) a base selected from the group consisting of an alkali metal hydroxide, an alkali metal carbonate and an amine, by means of a member selected from the group consisting of hydrogen gas, formic acid, and hydrazine, at a reaction temperature of from room temperature to 150° C. under atmospheric pressure or elevated pressure.

3. The process according to claim 2, wherein the reduction reaction is conducted in the presence of a base selected from the group consisting of an alkali metal hydroxide and a tertiary amine by means of hydrogen gas under hydrogen gas pressure.

4. The process according to claim 1, wherein the reaction of the aniline compound with hydrogen is conducted by means of a member selected from the group consisting of hydrogen gas, formic acid and hydrazine.

* * * * *